United States Patent
Yerike

(10) Patent No.: US 11,020,357 B2
(45) Date of Patent: Jun. 1, 2021

(54) COMPOUND FOR USE IN RELIEF OF PAIN AND METHOD TO PRODUCE THEREOF

(71) Applicant: Alexandra Yerike, Beverly Hills, CA (US)

(72) Inventor: Alexandra Yerike, Beverly Hills, CA (US)

(*) Notice: Subject to any disclaimer, the term of this patent is extended or adjusted under 35 U.S.C. 154(b) by 0 days.

(21) Appl. No.: 16/358,623

(22) Filed: Mar. 19, 2019

(65) Prior Publication Data
US 2019/0282513 A1  Sep. 19, 2019

Related U.S. Application Data

(60) Provisional application No. 62/644,854, filed on Mar. 19, 2018.

(51) Int. Cl.
| | |
|---|---|
| *A61K 31/045* | (2006.01) |
| *A61P 25/04* | (2006.01) |
| *A61K 31/05* | (2006.01) |
| *A61K 31/08* | (2006.01) |
| *A61P 29/00* | (2006.01) |
| *A61K 9/00* | (2006.01) |
| *A61K 31/085* | (2006.01) |

(52) U.S. Cl.
CPC ............ *A61K 31/05* (2013.01); *A61K 9/0014* (2013.01); *A61K 31/08* (2013.01); *A61K 31/085* (2013.01); *A61P 29/00* (2018.01)

(58) Field of Classification Search
CPC ............................. A61K 31/045; A61P 25/04
USPC ......................................................... 514/730
See application file for complete search history.

(56) References Cited

U.S. PATENT DOCUMENTS

| | | | |
|---|---|---|---|
| 5,260,313 A | | 11/1993 | Frome |
| 5,716,928 A | * | 2/1998 | Benet ................... A61K 36/899 424/409 |
| 6,264,995 B1 | | 7/2001 | Newmark et al. |
| 6,403,126 B1 | | 6/2002 | Webster et al. |
| 6,949,582 B1 | | 9/2005 | Wallace |
| 9,375,417 B2 | | 6/2016 | Smith et al. |
| 2002/0111377 A1 | | 8/2002 | Stinchcomb |
| 2007/0003536 A1 | | 1/2007 | Zimmerman |
| 2009/0247619 A1 | * | 10/2009 | Stinchcomb ......... A61K 9/0014 514/454 |
| 2010/0099766 A1 | * | 4/2010 | Zhang ................. A61K 9/0014 514/567 |
| 2017/0348276 A1 | * | 12/2017 | Bryson .................... A61K 9/06 |

OTHER PUBLICATIONS

"Top 15 Powerful Turmeric Essential Oil Uses and Benefits", Up Nature, published Sep. 25, 2017.*
Russo, Ethan B., Cannabinoids in the management of difficult to treat pain, Therapeutics and Clinical Risk Management, Feb. 2008, 4(1): 245-259., Dove Medical Press Limited, Published online.
Hur, MH, Aromatherapy massage on the abdomen for alleviating menstrual pain in high school girls: a preliminary controlled clinical study, Evidence-Based Complementary and Alternative Medicine, 2012, PMID: 21949670 PMCID: PMC3178179 DOI: 10.1155/2012/187163, Hindawi Publishing Corporation, Published online.
Lucas, L, Molecular mechanisms of inflammation. Anti-inflammatory benefits of virgin olive oil and the phenolic compound oleocanthal, Current Pharmaceutical Design, 2011, 17(8):754-68, Bentham Science Publishers, Published online.
Intahphuak, S., Anti-inflammatory, analgesic, and antipyretic activities of virgin coconut oil, Pharmaceutical Biology, Feb. 2010, (2):151-7, DOI: 10.3109/13880200903062614, Informa, Published online.
Costa, Barbara, The non-psychoactive cannabis constituent cannabidiol is an orally effective therapeutic agent in rat chronic inflammatory and neuropathic pain, European Journal of Pharmacology, Feb. 5, 2017, vol. 556, Issues 1-3. pp. 75-83, Elsevier, Published online.

* cited by examiner

*Primary Examiner* — Raymond J Henley, III
(74) *Attorney, Agent, or Firm* — Milord A. Keshishian

(57) ABSTRACT

This present invention provides a composition for use in relief of pain and method of production thereof. The composition comprises cannabidiol (CBD) powder, ethoxydiglycol, essential oils and warming agents. The composition is applied topically to relieve pain, specifically the pain associated with menstrual cramps.

9 Claims, 1 Drawing Sheet

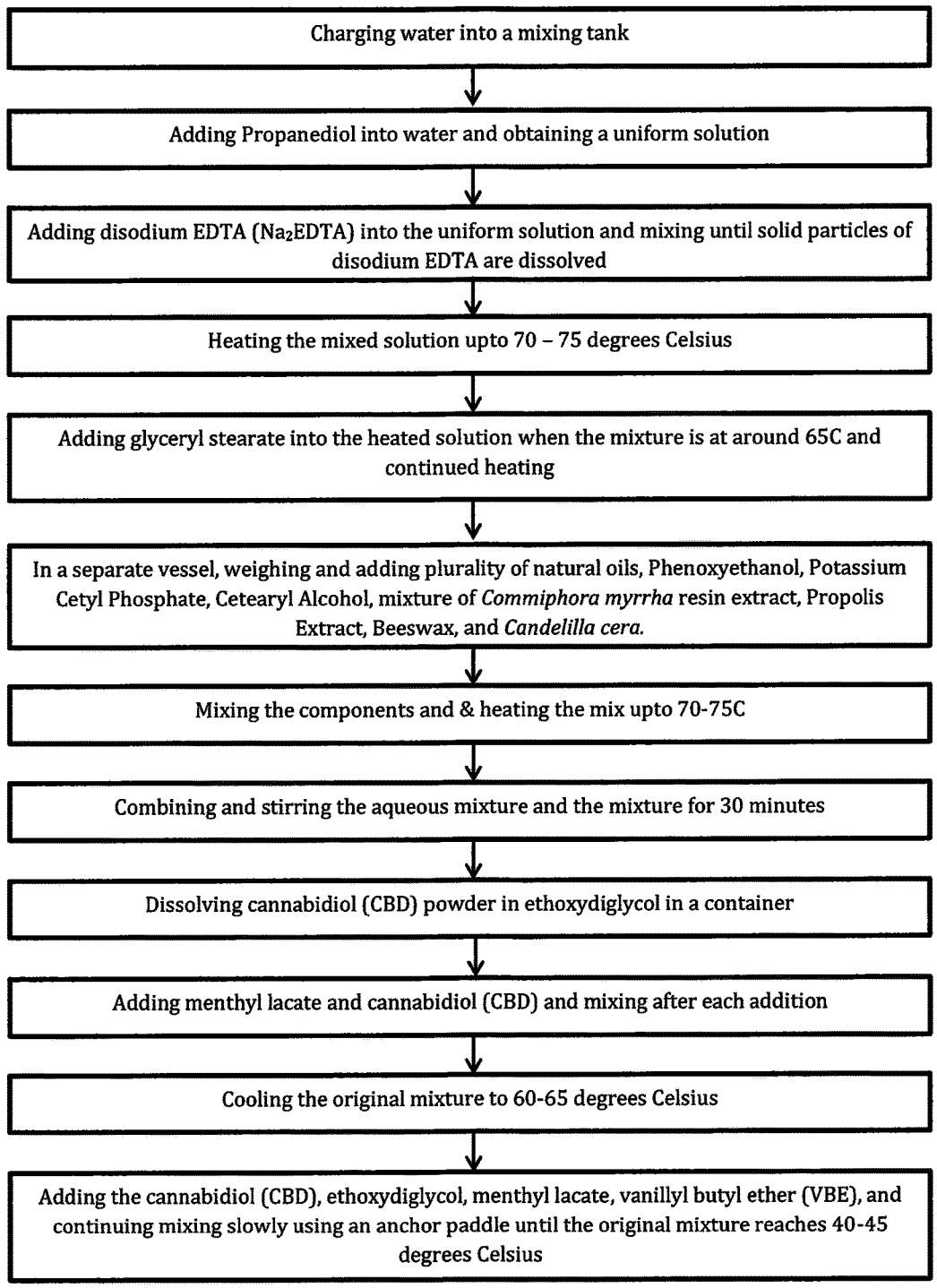

COMPOUND FOR USE IN RELIEF OF PAIN AND METHOD TO PRODUCE THEREOF

CROSS-REFERENCE TO RELATED APPLICATIONS

This Application claims the benefit of priority of the U.S. Utility Provisional Patent Application 62/644,854, with a filing date Mar. 19, 2018, the entire disclosure of which is expressly incorporated by reference in its entirety herein. It should be noted that where a definition or use of a term in the incorporated patent application is inconsistent or contrary to the definition of that term provided herein, the definition of that term provided herein applies and the definition of that term in the incorporated patent application does not apply.

BACKGROUND OF THE INVENTION

1. Field of the Invention

The present invention, generally, relates to a composition for facilitating a pain relief, more particularly, the present invention relates to a composition comprising ethoxyglycol, cannabidiol (CBD) and essential oils for providing relief from menstrual pain.

2. Background and Related Art

Typically, women, during their mentrual periods, suffer from dysmenorrhea, or menstrual cramps, which cause throbbing pain in the lower abdomen. The severity of pain can range from being merely annoying to being severe enough to disrupt daily activities. Approximately 30% of women suffer from cramps severe enough to interfere with their daily activities. In 10% of women, this pain is severe enough to disrupt their lives. Women commonly relieve cramps by taking over-the-counter pain relievers such as ibuprofen and naproxen sodium. Hormonal birth control is often prescribed to women with more severe cramps.

In the past, women have treated their cramps with various herbal remedies such as the cannabis plant. The cannabis plant contains over 100 active compounds known as cannabinoids. One of the most abundant of these compounds is cannabidiol (CBD). CBD lacks the psychoactive effects of tetrahydrocannabinol (THC) but has shown significant medical benefits. CBD is an active ingredient of the drug Nabiximols, which has been approved in Canada to treat the pain associated with multiple sclerosis. A drug called Epidiolex, which is purified liquid CBD, is currently under FDA approval for the treatment of certain types of epilepsy. CBD is also an anti-inflammatory, which means it can effectively treat pain.

In prior art, there have been several attempts to manufacture a topical formula used for pain relief with CBD as the active ingredient.

U.S. Pat. No. 6,949,582 to Wallace discloses a rapid-onset cannabinoid delivery topical liniment which utilizes a combination of cannabinoids, flavonoids, terpenoids, and other constituents extracted from herbal cannabis, that mimic the body's own endocannabinoids and interact selectively and synergistically with presently known cannabinoid receptors CB1 and CB2 to contribute important analgesic, anti-inflammatory, and other useful effects.

A study in *Therapeutics and Clinical Risk Management* (Russo, 2008 February; 4(1): 245-259) showed that CBD was an effective anti-inflammatory analgesic for treating cancer-related pain. A 2007 study in the *European Journal of Pharmacology* showed that CBD effectively treated chronic pain when taken orally. (Costa, et al., 5 Feb. 2007; 556(1-3): 75-83).

U.S. Pat. No. 9,375,417 to Smith et al. discloses the use of CBD in an ointment that can be applied topically for the treatment of pain. U.S. Pat. No. 6,403,126 to Webster et al. describes a method for extracting CBD from the cannabis plant and also discloses that CBD may be effective for the treatment of menstrual cramps.

Techniques for the extraction of CBD from the cannabis plant are well-known. Pure CBD powder is sold commercially by various wholesalers, such as Entourage and Hemp Health, Inc. Smith, et al. and Wallace described formulas using CBD for pain relief that relied on CBD and other cannabinoids but did not combine analgesic properties of CBD with the therapeutic properties of essential oils. The essence of certain plants can be extracted from the fragrant part of the plant, typically the bark, leaves, flowers, resin, or peel; wherein distillation is the most common method for extracting these essential oils from the plants. The distilled essential oil is a lipophilic mixture of volatile compounds such as esters, ketones, aldehydes, and phenols. Traditional folk medicine has used these oils for healing a multitude of ailments. The first recorded use of essential oils in medicine dates back to the 10th century. Essential oils have treated coughs, stomach ailments, and some essential oils have antiseptic qualities. Further, some oils such as peppermint oil, geranium oil, and clary sage oil relieve pain when applied topically.

Therefore, there is a need for a composition that combines the analgesic properties of CBD with the therapeutic effects of essential oils into an ointment that can be applied topically for the treatment of pain.

BRIEF SUMMARY OF THE INVENTION

A non-limiting, exemplary aspect of an embodiment of the present invention provides a composition comprising cannabidiol powder, ethoxydiglycol, water, warming agent, plurality of natural and essential oils.

A non-limiting, exemplary aspect of an embodiment of the present invention provides a method of relieving pain by application of the composition comprising cannabidiol powder, ethoxydiglycol, water, warming agent, plurality of natural and essential oils. The method comprises topically administering the composition over the area of pain.

A non-limiting, exemplary aspect of an embodiment of the present invention provides a method of preparation of the composition for relieving pain.

In accordance with a still further non-limiting, exemplary aspect of an embodiment of the present provides a method of relieving pain, specifically a menstrual pain.

Accordingly, an advantage of the present invention is the combination of analgesic properties of CBD with the therapeutic effects of essential oils into an ointment that can be applied topically for the treatment of pain, specifically the pain associated with menstrual cramps.

BRIEF DESCRIPTION OF THE DRAWINGS

It is to be understood that the drawings are to be used for the purposes of exemplary illustration only and not as a definition of the limits of the invention. Various embodiments will hereinafter be described in accordance with the appended drawings, which are provided to illustrate, not limit, the scope, wherein similar designations denote similar elements, and in which:

FIG. 1 illustrates a flowchart of the method for production of the composition of present invention for relieving pain, in accordance with at least one of the embodiments.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Further, the terms "a" and "an" herein do not denote a limitation of quantity, but rather denote the presence of at least one of the referenced items. Moreover, various features are described which may be exhibited by some embodiments and not by others. Similarly, various requirements are described which may be requirements for some embodiments but not for other embodiments.

The embodiments are described herein for illustrative purposes and are subject to many variations. It is understood that various omissions and substitutions of equivalents are contemplated as circumstances may suggest or render expedient but are intended to cover the application or implementation without departing from the spirit or the scope of the present disclosure. Further, it is to be understood that the phraseology and terminology employed herein are for the purpose of the description and should not be regarded as limiting. Any heading utilized within this description is for convenience only and has no legal or limiting effect.

When used herein, the term "topical administration" or "topical application" refers to administration of a composition by comprising intact skin or a pharmaceutical composition intradermal administration. For example, by rubbing the composition of the present invention on an area of intact skin or by placing on an area of intact skin compositions of the invention comprising a patch of the skin.

The term "topical composition" refers to topical administration and is designed to contain a pharmaceutical composition. The composition can be present in various forms selected from ointments, creams, lotions, pastes, gels and the like.

The present disclosure, in general, describes a composition for use in relief of pain. The compound comprises water, ethoxydiglycol, cannabidiol (CBD) powder, a plurality of essential oils and a plurality of natural oils; and vanillyl butyl ether (VBE). Further, the composition is applied topically to relieve pain, specifically the pain associated with menstrual cramps.

The present invention discloses an ointment comprising CBD, essential oil(s), natural oil(s), moisturizer(s), preservative(s), chelating agent(s), warming agent(s), and cooling agent(s).

In an embodiment, the composition comprises water in an amount by weight in the range of 70-75 percent, ethoxydiglycol in the range of 2-3 percent, cannabidiol (CBD) powder in the range of 0.020 to 0.030 percent, and more preferably, in the range of 0.025 to 0.030 percent and vanillyl butyl ether (VBE) in the range of 0.020-0.030 percent.

The combination of CBD powder and ethoxydiglycol opens up nerve endings and acts as a pain mediator. The combination of ethoxydiglycol, CBD powder, and essential oils makes the present composition a potent blend for pain relief. The combination of ethoxydiglycol, CBD powder, and VBE works on nerve endings for a more pronounced pain relief. The combination of ethoxydiglyclol, CBD, essential oils and VBE creates an especially potent pain relief.

Generally, ethoxydiglycol sold under the trade name of Transcutol CG, acts as a solvent and a penetration enhancer. The component is found in hair products, makeup and bath products. It ensures a uniform mixture of the ingredients of the invention. Further, ethoxydiglycol acts as a cosurfactants for microemulsions.

In the topical composition of the invention, CBD powder is an active ingredient. The preferred embodiment contains approximately 0.028% CBD powder by weight. Further, clinical studies have shown that CBD powder is an effective anti-inflammatory agent.

The plurality of essential oils is selected from but not limited to *Cannabis sativa* seed oil, C12-18 alkyl glucoside, glyceryl stearate, cerearyl alcohol, stearic acid, pelargonium, and graveolens flower oil (geranium oil), *Lavender angustifia* (lavender oil), *Salvia sclarea* oil (clary sage oil), *Eugenia caryophyllus* flower oil (clove bud oil), *Citrus aurantium bergamoa* fruit oil (bergamot oil), and *Mentha piperita* oil (peppermint oil).

In an exemplary embodiment, the present composition utilizes emulsifiers such as Hempseed Emulsipure® which is a trade name of a mixture of *Cannabis sativa* seed oil, C12-18 alkyl glucoside, glyceryl stearate, cetearyl alcohol, stearic acid. Hempseed Emulsipure®, potassium cetyl phosphate, and cetearyl alcohol act as emulsifiers. The Hempseed Emulsipure® contains fats and essential fatty acids which also act as emulsifiers. It contains vitamin E, phosphorus, potassium, sodium, magnesium, sulfur, calcium, iron, and zinc. Further, the Hempseed Emulispure® also acts as a source of CBD. Potassium cetyl phosphate, which is trademarked as Amphisol K, is a powder that acts as a waterproofing agent and emulsifier and is commonly found in sunscreens. Cetearyl alcohol is a long chain of organic alcohol that acts as an emulsifier and increases viscosity. In some embodiments of the invention, fatty alcohols or fatty acids, such as stearic acid, cetyl alcohol, and stearyl alcohol can act as an emulsifier in place of the Hempseed Emulsipure®.

The plurality of natural oils is selected from but not limited to *Olea europeaea* fruit oil; and cocosnucifera oil. In an exemplary embodiment, the *Olea europeaea* fruit oil is olive oil, and cocosnucifera oil is coconut oil. Olive oil contains oleocanthal, which acts as an anti-inflammatory agent. A study in Current Pharmaceutical Design (Lucas, et al. 2011; 17(4754-68)) showed that oleocanthal has anti-inflammatory properties similar to ibuprofen. Coconut oil has many health benefits. A study in Pharmaceutical Biology (Intahphuak, et al. 2010 February; 48(2):151-7) suggests that there may be anti-inflammatory properties to coconut oil. In some embodiments of the invention, other natural oils may be used instead of olive oil and/or coconut oil.

In a preferred embodiment, the composition comprises a moisturizer. The moisturizer used is Zemea® which is a trade name for 1,3-propanediol. Zemea® can also act as a solvent in place of ethanol, hexane, or propylene glycol. It also acts a surfactant and a preservative. In alternate embodiments of the composition, diols, such as butylene glycol, hexylene glycol, pentylene glycol, and glycols, such as hexane diol and hydrolite 6, can be used in place of Zemea®.

In an embodiment, the composition comprises Procolor DC which is a mixture of *Commiphora myrrha* resin extract, propolis extract, beeswax, and *Candelilla cera*. In the preferred embodiment of the composition, Procolor DC aids in permeation of the CBD powder.

In an embodiment, the composition comprises preservative(s), preferably, AE Protek Plus, which is manufactured by AE Chemie, and contains phenoxyethanol and ethyihexylglycerin. In alternative embodiments, parabens may be used as a preservative in place of AE Protek Plus.

In an embodiment, the composition comprises a cooling agent(s), preferably, AE Chemiekool Plus made by AE Chemie that consists of menthyl lactate and methahaplocalix. In alternative embodiments of the composition, menthols may be used in place of AE Chemiekool Plus.

In a preferred embodiment, disodium ethylenediaminetetraacetic acid (EDTA) is used as a preservative and chelating agent. It removes ions found in hard water, preserving the life of the ointment. It is a common ingredient found in cosmetics, shampoos, and sunscreens. In some embodiments, other natural chelating agents, such as tetrasodium glutamate diacetate, can be used as a substitute for disodium EDTA.

In a further preferred embodiment, vanillyl butyl ether acts as a warming agent. In an alternative embodiment, capsaicin can be used as a substitute for vanillyl butyl ether.

In another preferred embodiment of the invention, the composition contains the essential oils of clove bud oil, lavender oil, bergamot oil, geranium oil, peppermint oil, turmeric, and clary sage oil. Other embodiments of the present composition may have a different combination of these essential oils. Further embodiments of the composition may include ginger oil, rosemary oil, juniper oil, tea tree oil, chamomile in the essential oil mixture.

Clove bud oil is extracted from the flowers of the clove tree, *Syzygium aromaticum*. It is used in homeopathic remedies, primarily associated with dental care. It acts as an antifungal and antibiotic agent. It had been shown to relieve sore throats, toothaches, and gum diseases. It has also been used topically to heal wounds and cuts.

The lavender essential oil is extracted from the flowers of lavendulan plants. It is used in massage oils to aid in the relief of backaches and joint pain, and its ability to eliminate nervous tension and enhance blood circulation. Lavender oil is an effective analgesic and anti-inflammatory and provided pain relief compared with the medication Tramadol. The aroma of lavender essential oil is calming, making it helpful in treating migraines, headaches, depression, tension, and stress.

Bergamot oil is derived from the rind of the bergamot orange fruit, *Citrus bergamia*. Some of the components of bergamot oil include alpha-pinene and limonene, which have shown stimulating and antidepressant effects. Because bergamot oil is fragrant and acts as an antibiotic, it is a common ingredient in organic deodorants. It can stimulate the secretion of hormones, which lessens the sensitivity of nerves to pain. The bergamot oil is sometimes used as a topical treatment for sore muscles and it can also be used to improve the circulation of the blood.

Geranium oil is extracted from the geranium plant. Geranium oil can also be used for balancing hormones, relieving stress, and improving circulation.

Peppermint oil is extracted from a hybrid mint plant. It contains menthol, menthone, and menthyl acetate. Peppermint oil was used in traditional medicine for the treatment of various ailments. The high menthol content gives it a cooling effect when applied topically, so it can be used to treat muscle and nerve pain.

Turmeric is a plant in the ginger family native to the Indian subcontinent. The active compound in the turmeric plant is curcumin. Ancient cultures on the Indian subcontinent used turmeric to treat indigestion, common colds and applied it topically to treat wounds and sores. Turmeric is used in various topical creams and ointments. Clary sage oil is distilled from the clary sage plant, a flowering plant native to the Mediterranean basin.

The present disclosure further discloses a method of preparation of the pain relief composition as illustrated in FIG. 1.

In an embodiment, the method comprises a step of filling water into a mixing tank and a step of adding propanediol into the water and obtaining a uniform solution. The method then comprises a step of adding disodium EDTA ($Na_2EDTA$) into the uniform solution and mixing until solid particles of disodium EDTA are dissolved. Then a step of heating the mixed solution to 60 degrees Celsius takes place. Further, the method comprises a step of adding *Cannabis sativa* seed oil, C12-18 Alkyl Glucoside, Glyceryl Stearate, Cetearyl Alcohol and Stearic acid into the heated solution and heating is continued until the mixed solution reaches 70-75 degrees to obtain an aqueous mixture.

Further, the method comprises a step of weighing and mixing a plurality of essential oils, a plurality of natural oils, phenoxyethanol, potassium cetyl phosphate, cetearyl alcohol, *Commiphora myrrha* resin extract, propolis extract, beeswax, and *Candelilla cera* to obtain a mixture. The method then comprises a step of mixing and heating the mixture to 70-75 degrees Celsius. Further, the method comprises a step of combining the aqueous mixture and the mixture for thirty (30) minutes.

Furthermore, the method comprises a step of dissolving cannabidiol (CBD) powder in ethoxydiglycol in a container, a step of adding menthyl lacate and cannabidiol (CBD) and mixing after each addition. The method then comprises a step of cooling the original mixture to 60-65 degrees Celsius. Then the method comprises a step of adding the cannabidiol (CBD), ethoxydiglycol, menthyl lacate, vanillyl butyl ether (VBE), and continuing mixing slowly using an anchor paddle until the original mixture reaches 40-45 degrees Celsius.

In another embodiment, the method of producing the composition of the invention comprises a step of charging water into a stainless-steel mixing vessel; a step of adding propanediol into the water and mixing until a homogenous solution is obtained. The method further comprises a step of adding disodium EDTA into the main vessel and mixing until the solution is homogenous to obtain a clear mixture. The solution is then heated to 70-75 degree Celsius. Then, with continued heating, glyceryl stearate is added when the temperature of the mixture is approximately 65 degree Celsius.

Further, a plurality of natural oils, phenoxyethanol, potassium cetyl phosphate, cetearyl alcohol, mixture of *Commiphora myrrha* resin extract, Propolis extract, Beeswax, and *Candelilla cera* are added in a separate stainless-steel vessel after weighing. The mixture is then heated up to 70-75 degree Celsius. When both the vessels reach to the desired temperature of 70-75 degree Celsius, the mixtures are combined with continuous stirring ensuring the mixtures are mixed properly. The heat source is turned off. Then in a separate stainless-steel vessel, plurality of essential oils is weighed out. The blend is cooled down to 60-65 degree Celsius and added to the main batch. Then the mixing of batches is continued for thirty (30) minutes.

Furthermore, in a separate stainless-steel vessel, cannabidiol (CBD) powder is dissolved into Ethoxydigylcol. Then menthyl lactate and vanillyl butyl ether are added keeping the mixture homogeneous. Further, CBD mixture is added to the main batch after cooling of the main batch to 45-50 degree Celsius. The mixing of the batches is continued until a homogeneous mixture is obtained and allowed to cool down to room temperature. The batch thickens overnight.

EXAMPLE

In a preferred embodiment of the present invention, the composition comprises the ingredients in the following weight percentages:

| Ingredient(s) | Amount (wt. %) |
| --- | --- |
| Water | 71.292 |
| Hempseed Emulsipure | 6.9 |
| Olive Oil | 3 |
| Ethoxydiglycol | 2.6 |
| Coconut Oil | 2.5 |
| Zemea | 2 |
| Procolor DC | 2 |
| AE Chemiekool Plus | 1.5 |
| Clove Bud Oil | 1.25 |
| Lavender Oil | 1.04 |
| AE Protek Plus | 1 |
| Potassium Cetyl Phosphate | 0.9 |
| Bergamot Oil | 0.87 |
| Geranium Oil | 0.76 |
| Peppermint Oil | 0.625 |
| Cetearyl Alcohol | 0.55 |
| Turmeric | 0.53 |
| Clary Sage Oil | 0.53 |
| CBD Powder | 0.028 |
| Vanillyl Butyl Ether (VBE) | 0.025 |

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms enclosed. On the contrary, the intention is to cover all modifications, alternative constructions, and equivalents falling within the spirit and scope of the invention, as defined in the appended claims. Thus, it is intended that the present invention cover the modifications and variations of this invention, provided they are within the scope of the appended claims and their equivalents.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

The invention claimed is:

1. A composition comprising:
    a cannabidiol (CBD) powder;
    an ethoxydiglycol;
    a warming agent;
    water; and
    a combination of a plurality of natural oils and a plurality of essential oils;
    wherein the plurality of natural oils further comprises: a combination of olive oil and coconut oil, and
    wherein the plurality of essential oils further comprises 1.25% (weight/weight) of clove bud oil, 1.04% (weight/weight) of lavender oil, 0.87% (weight/weight) of bergamot oil, 0.76% (weight/weight) of geranium oil, 0.625% (weight/weight) of peppermint oil, 0.53% (weight/weight) of turmeric oil, 0.53% (weight/weight) of clary sage oil.

2. The composition of claim 1, wherein the warming agent is vanillyl butyl ether (VBE).

3. The composition of claim 1, further comprising moisturizers, preservatives, chelating agents and/or cooling agents.

4. The composition of claim 1, wherein the cannabidiol (CBD) powder in the range of 0.020% (weight/weight) to 0.030% (weight/weight) of the composition.

5. The composition of claim 4, wherein the cannabidiol (CBD) powder is in the range of 0.025% (weight/weight) to 0.030% (weight/weight) of the composition.

6. The composition of claim 2, wherein the vanillyl butyl ether (VBE) is in the range of 0.020% (weight/weight) to 0.028% (weight/weight) of the composition.

7. The composition of claim 1, wherein the composition is administered topically.

8. The composition of claim 1, wherein the plurality of natural oils further comprises 3% (weight/weight) of the olive oil and 2.5% (weight/weight) of the coconut oil.

9. The composition of claim 3, wherein the chelating agent is any one selected from disodium ethylenediaminetetraacetic acid (EDTA), tetrasodium glutamate diacetate and alike chelating agent.

* * * * *